(12) United States Patent
Klaffenböck et al.

(10) Patent No.: US 10,932,773 B2
(45) Date of Patent: Mar. 2, 2021

(54) DEVICE FOR CONNECTING BODY TISSUES

(71) Applicants: Johann Klaffenböck, Strobl (AT);
Lukas Klaffenböck, Strobl (AT);
Julian Mair, Munich (DE)

(72) Inventors: Johann Klaffenböck, Strobl (AT);
Lukas Klaffenböck, Strobl (AT);
Julian Mair, Munich (DE)

(*) Notice: Subject to any disclaimer, the term of this patent is extended or adjusted under 35 U.S.C. 154(b) by 133 days.

(21) Appl. No.: 16/342,479

(22) PCT Filed: Oct. 17, 2017

(86) PCT No.: PCT/AT2017/060264
§ 371 (c)(1),
(2) Date: Apr. 16, 2019

(87) PCT Pub. No.: WO2018/071932
PCT Pub. Date: Apr. 26, 2018

(65) Prior Publication Data
US 2020/0046347 A1    Feb. 13, 2020

(30) Foreign Application Priority Data

Oct. 17, 2016   (AT) .............................. A 50932/2016

(51) Int. Cl.
*A61B 17/068*    (2006.01)
*A61B 17/00*     (2006.01)

(52) U.S. Cl.
CPC .... *A61B 17/0684* (2013.01); *A61B 17/00234* (2013.01); *A61B 2017/00296* (2013.01);
(Continued)

(58) Field of Classification Search
CPC ............ A61B 17/0684; A61B 17/0682; A61B 17/1285; A61B 2017/00539
See application file for complete search history.

(56) References Cited

U.S. PATENT DOCUMENTS 3,650,453 A * 3/1972 Smith, Jr. .......... A61B 17/0684
                                                         227/138
4,523,695 A * 6/1985 Braun ................ A61B 17/0684
                                                         227/8
(Continued)

FOREIGN PATENT DOCUMENTS

EP          0040157 B1    3/1986

*Primary Examiner* — Andrew M Tecco
(74) *Attorney, Agent, or Firm* — Dykema Gossett PLLC

(57) ABSTRACT

A device for connecting body tissues has a head part, which can be pushed into a body opening and has a longitudinal axis, wherein tissue staples are accommodated in the head part in a storage position. The tissue staples have a linear main section and two engagement sections projecting perpendicularly therefrom aligned in a first plane perpendicular to the longitudinal axis. Optimal usability in the human body is achieved by rotor elements, which are pivotable about an axis parallel to the main sections of the tissue staples with each have a bearing surface for an engagement section of a tissue staple to rotate said tissue staple from the storage position into a working position in which the tissue staple is arranged in a further plane oriented perpendicularly to the first plane, and in that a slider is provided to advance the tissue staple and deform it into a clamping position.

26 Claims, 9 Drawing Sheets

(52) U.S. Cl.
CPC ............... *A61B 2017/00398* (2013.01); *A61B 2017/00539* (2013.01)

(56) References Cited

U.S. PATENT DOCUMENTS

| | | | | |
|---|---|---|---|---|
| 4,691,853 A | * | 9/1987 | Storace | A61B 17/0684 227/19 |
| 5,022,579 A | | 6/1991 | Matsutani et al. | |
| 5,170,926 A | * | 12/1992 | Ruckdeschel | A61B 17/0684 227/177.1 |
| 5,240,164 A | * | 8/1993 | Murray | A61B 17/0684 227/175.3 |
| 5,564,615 A | * | 10/1996 | Bishop | A61B 17/0682 227/175.1 |
| 7,458,494 B2 | | 12/2008 | Matsutani et al. | |
| 8,523,040 B2 | * | 9/2013 | Crainich | A61B 17/0684 227/175.1 |
| 2009/0272783 A1 | * | 11/2009 | Crainich | A61B 17/0401 227/176.1 |

\* cited by examiner

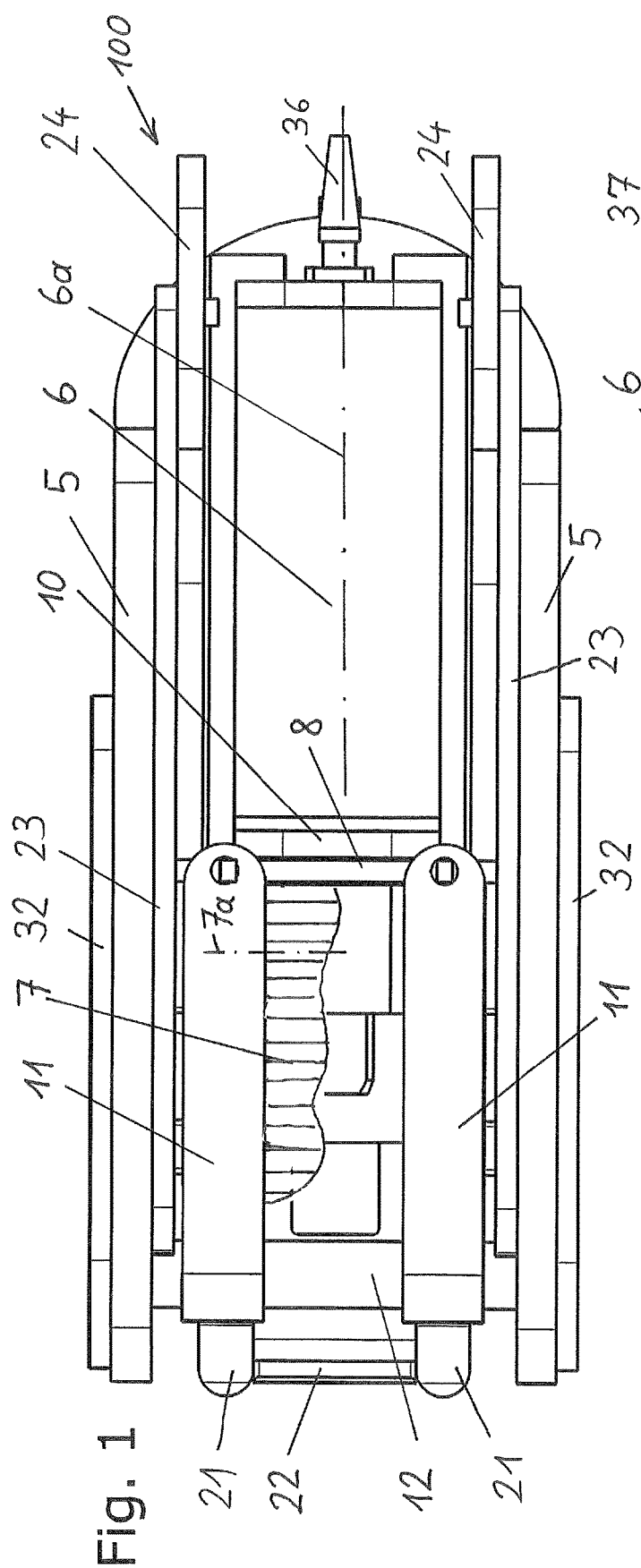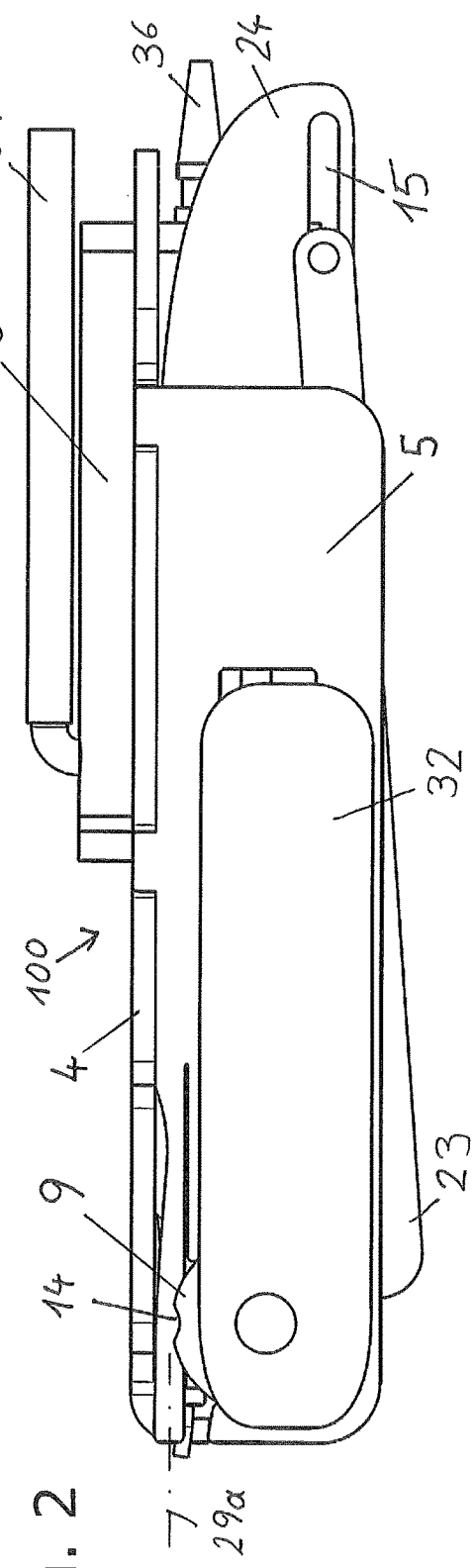

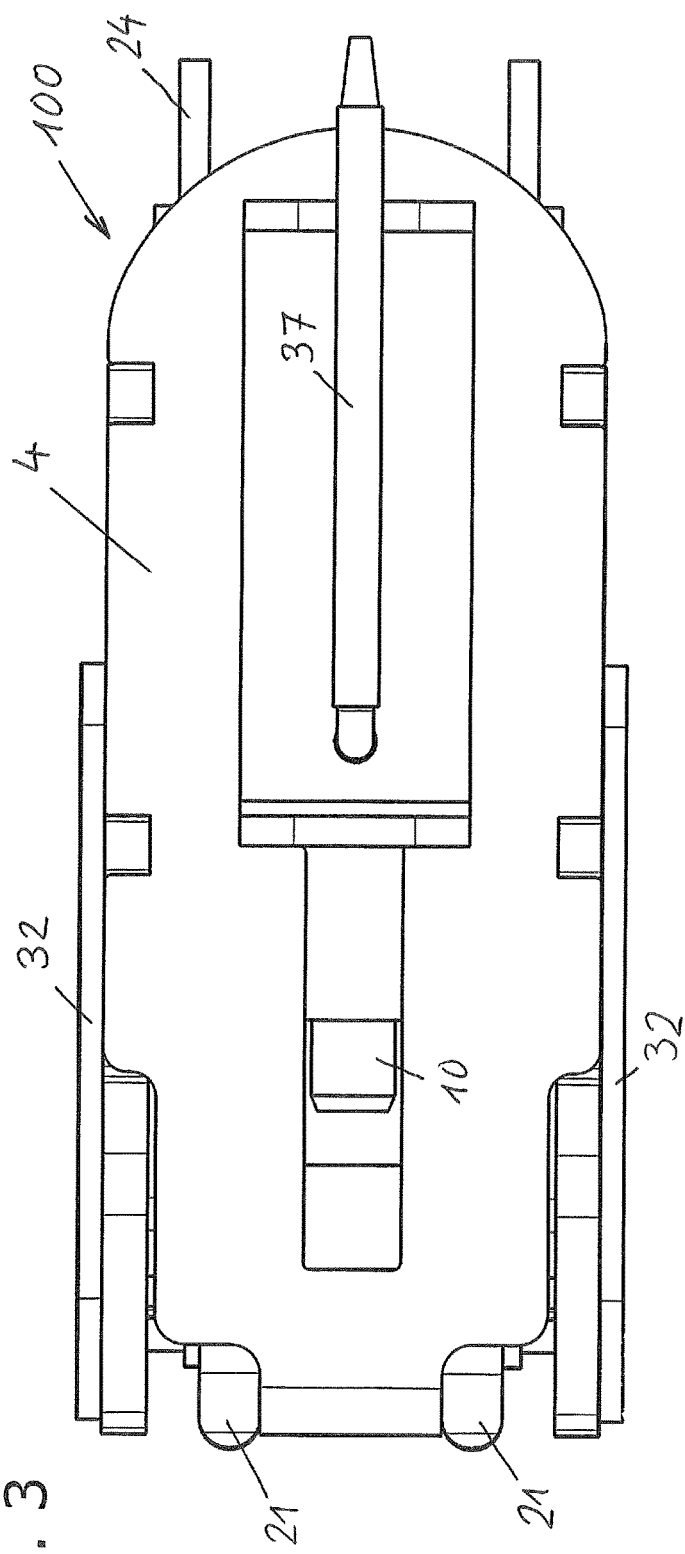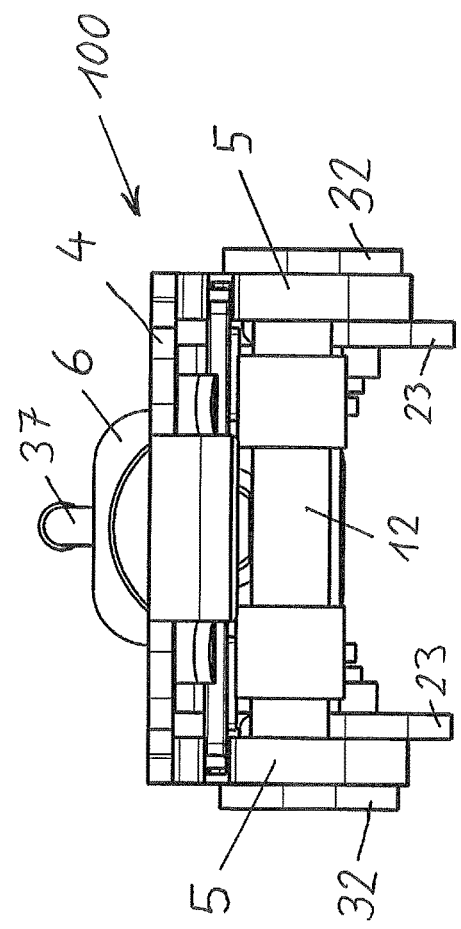
Fig. 3
Fig. 4

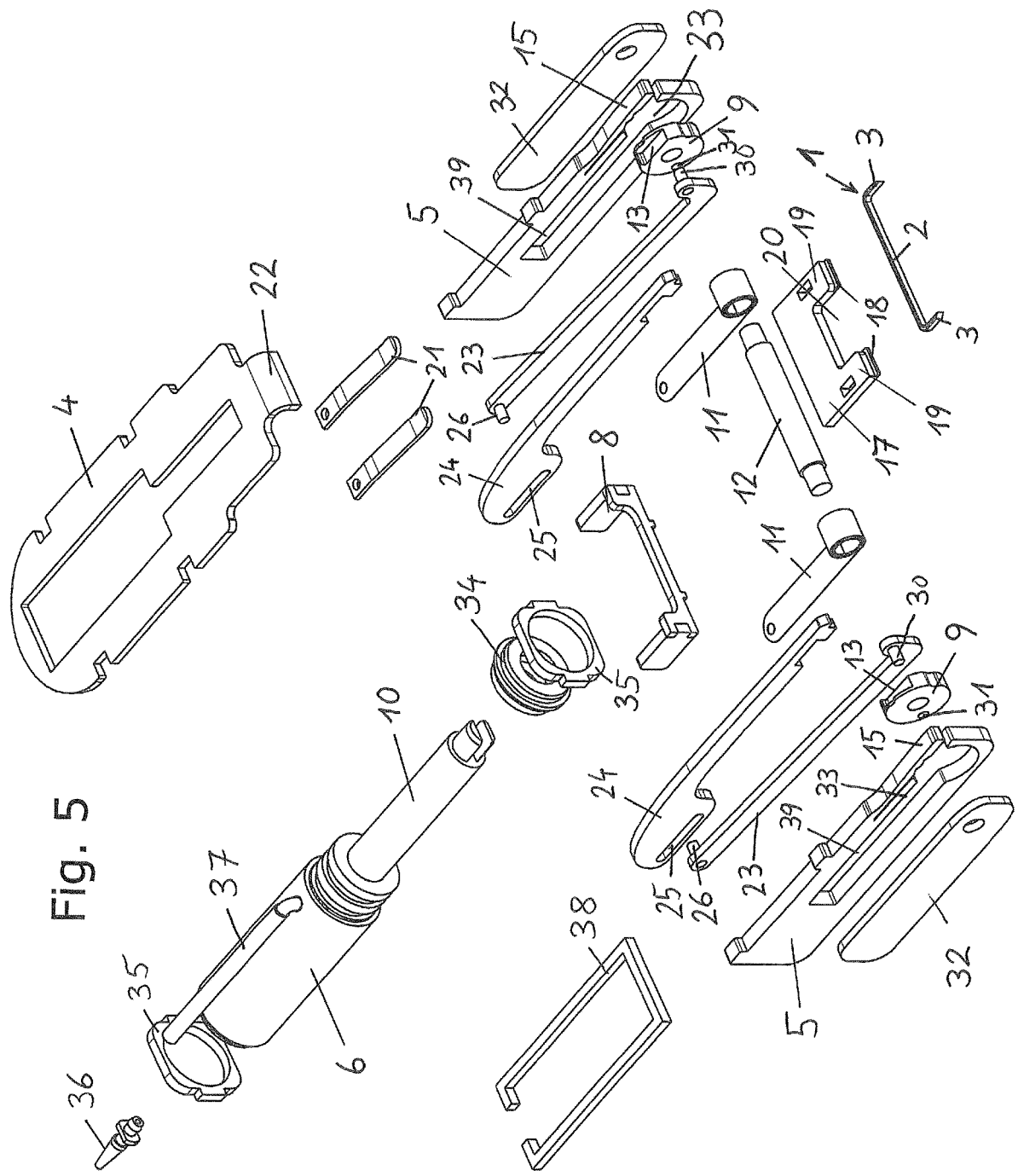

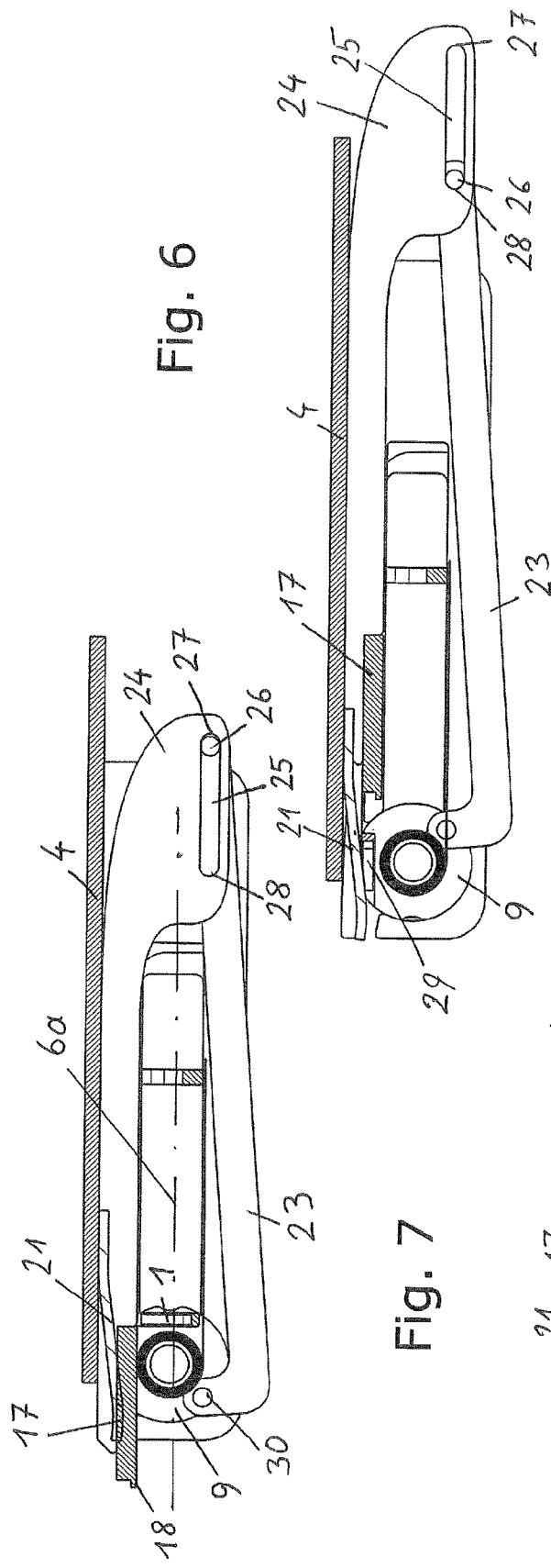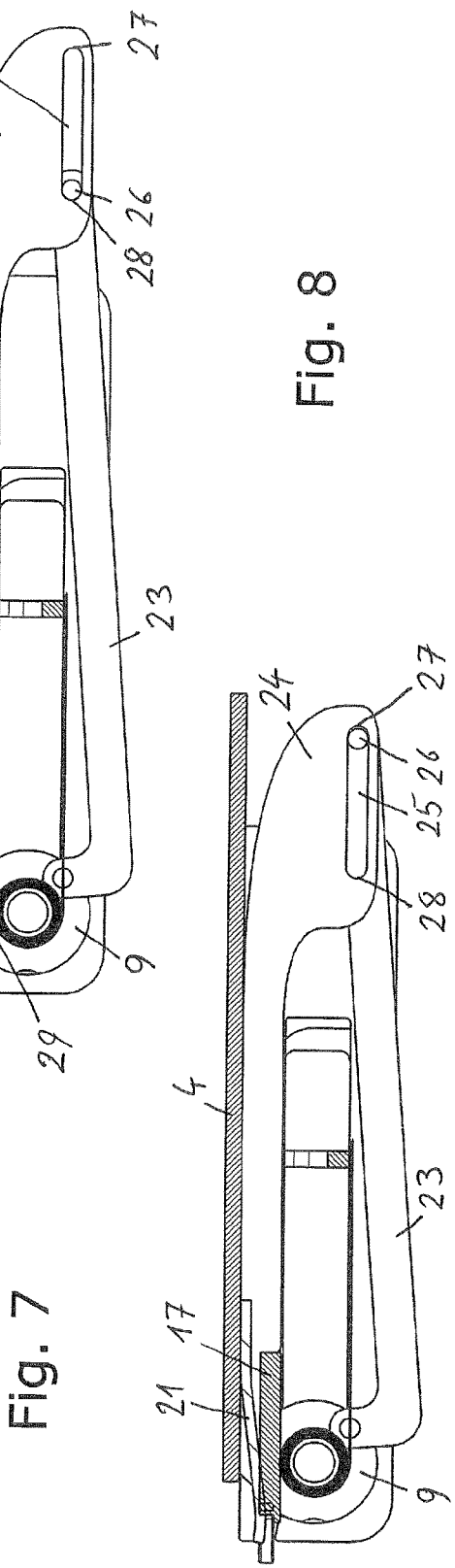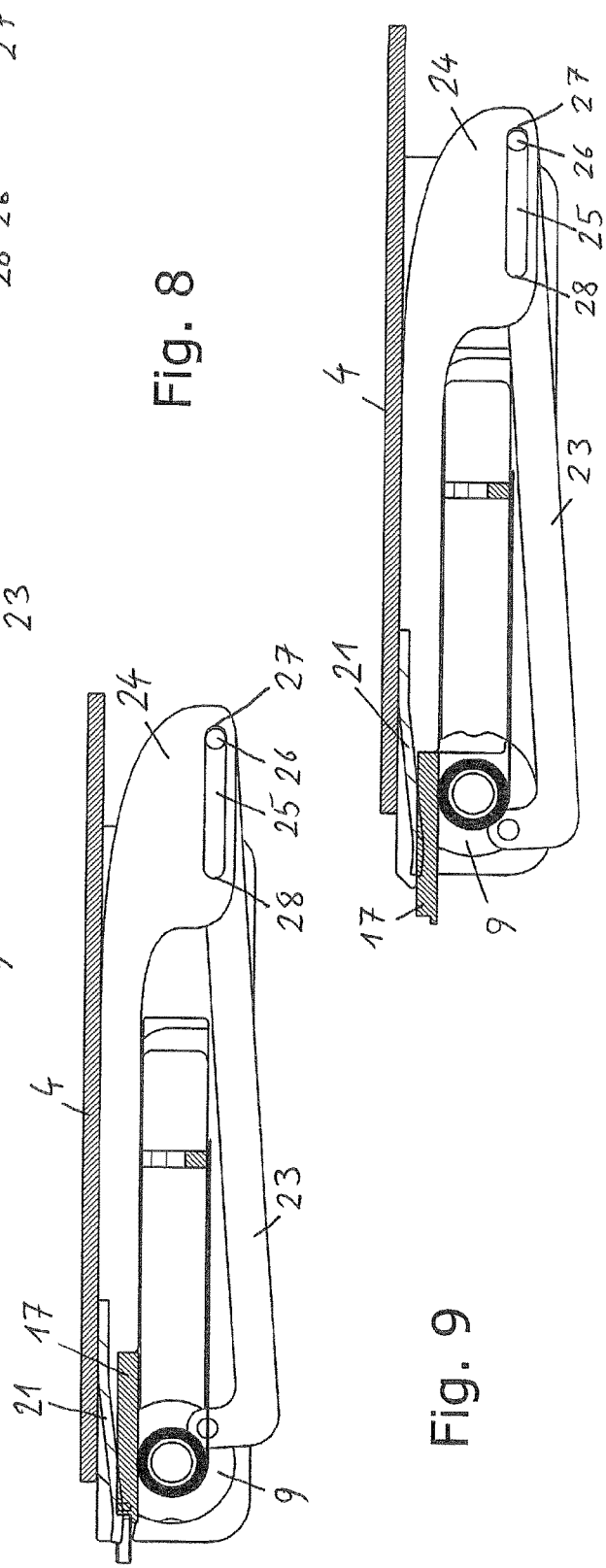

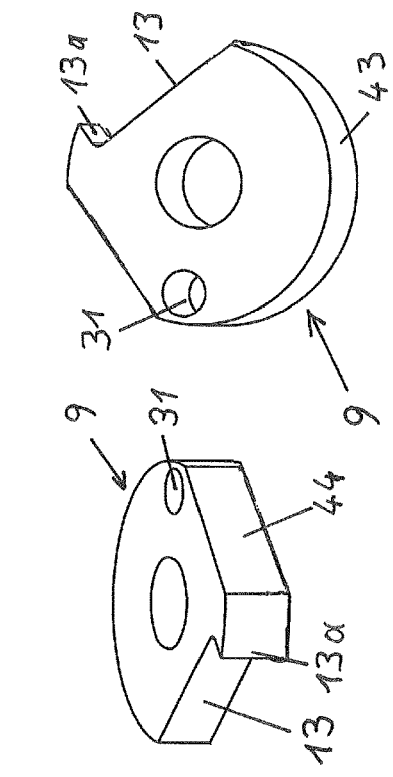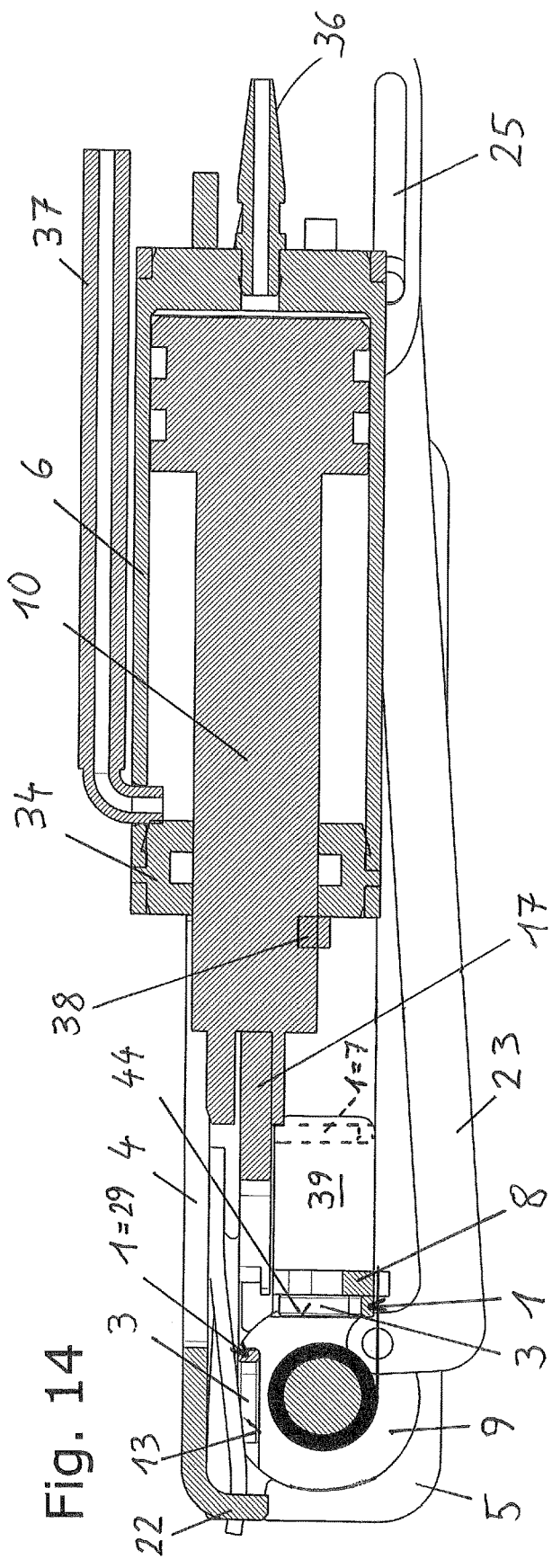

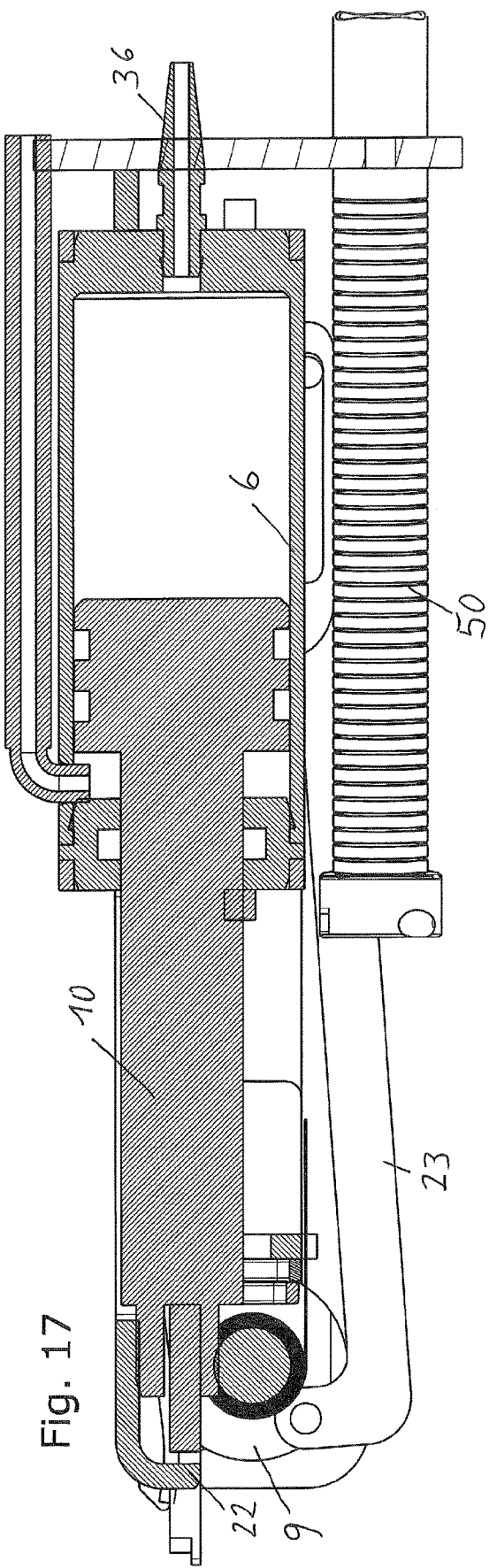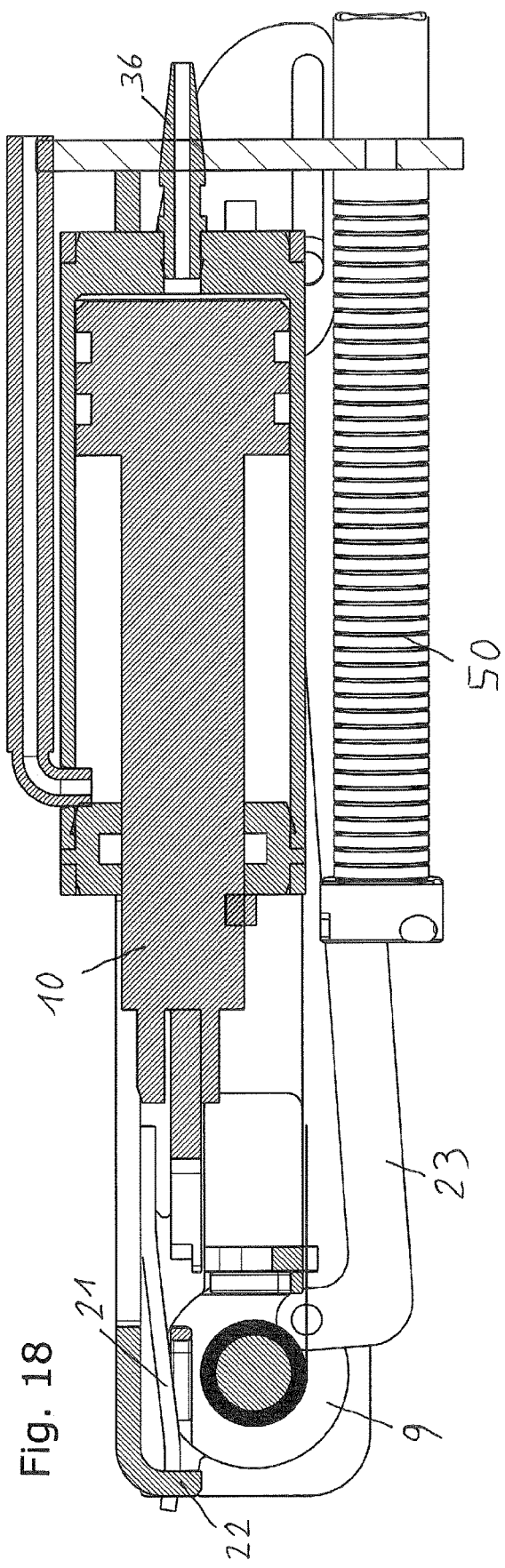

DEVICE FOR CONNECTING BODY TISSUES

CROSS-REFERENCE TO RELATED APPLICATIONS

This application is a national stage filing based upon International PCT Application No. PCT/AT2017/060264, filed 17 Oct. 2017, which claims the benefit of priority to Austria application No. A 50932/2016, filed 17 Oct. 2016.

BACKGROUND

The present invention relates to a device for connecting body tissues, having a head part with a longitudinal axis which can be pushed into a body orifice, wherein, in the head part, a plurality of tissue staples are accommodated in a storage position, which consist of a linear main section and two engaging sections projecting perpendicularly therefrom and which are each aligned in a first plane which is substantially perpendicular to the longitudinal axis.

It is known in medicine to close wounds with tissue staples, which are inserted into the skin in the area of the wound edges and then deformed in order to fix the wound edges against each other. Devices have been developed to carry out this process, which are generally referred to as staplers. Such devices are described in U.S. Pat. No. 5,170, 926 A, EP 1 695 668 A or EP0 354 724 B, for example. Typically, several tissue staples are stacked in a magazine, similar to paper staples. Before use, the foremost tissue staple is turned into a position in which it can be advanced and inserted into the skin.

The present invention relates to devices suitable for connecting sections of body tissue of the type described above, with the difference, however, that the device is sufficiently small and compact to be inserted into artificial or natural body orifices in order to connect body tissue inside the body. It therefore relates to the use in endoscopic or laparoscopic interventions. The particular requirement is therefore to design the device with the smallest possible cross-section, to safely apply the necessary actuating forces and to guarantee a high level of reliability, since direct visual and tactile control is not possible in this form of application.

Various devices for connecting body tissues inside the body have become known. However, these devices are complex to use and often only suitable for special applications.

SUMMARY OF THE INVENTION

It is the object of the present invention to create a simple and easy-to-use device that can be used to connect body tissue inside the body.

In accordance with the invention, two rotor elements are provided which are pivotable about an axis parallel to the main sections of the tissue staples and which each have a bearing surface for an engagement section of a tissue staple in order to rotate the said tissue staple from the storage position into an operating position in which the tissue staple is arranged in a further plane which is oriented substantially perpendicularly to the first plane, and a slider is provided in order to advance the tissue staple present in the operating position in the further plane and to deform it into a clamping position.

It is an essential aspect of this invention that the individual tissue staples are actively rotated by rotor elements from the plane in which they are stacked in the magazine (storage position) to the plane in which they are advanced to penetrate the body tissue (working position).

The rotation takes place about an axis, which is perpendicular to the longitudinal axis of the device and to the feed direction of the tissue staples.

A further important aspect of this invention is that a slider assumes the task of advancing a tissue staple as well as the task of deforming it after penetrating the body tissue in order to establish a secure connection. In this way, the number of components required can be kept to a minimum and the device can be designed to be particularly compact.

It is advantageous if a rotor spring acts on one rotor element in each case in order to make its movement latchable in two rotational positions, and that the rotor elements are preferably connected to a shaft. In this way it is possible to make the drive of the rotor elements simple and provide it with sufficient tolerances, since the exact angular position of the rotor elements in the critical positions, i.e. the reception and delivery of the tissue staples, is guaranteed by the latching.

A particularly elegant way of ensuring the feed of the tissue staples in the magazine and the necessary contact force on the rotor elements is to pretension the tissue staples in the storage position against the rotor element by at least one storage spring via a storage slider, wherein the storage spring preferably is attached to the shaft of the rotor elements. The storage spring is a leaf spring which is pretensioned into the wound position. It always strives to shorten the linear section parallel to the magazine and wind itself around the shaft. The particular advantage of this solution is that the force applied to the storage slider is independent of the position of the storage slider, i.e. said force remains essentially the same from the first to the last tissue staple.

A particularly high degree of compactness can be achieved by the rotor elements being driven by at least one connecting rod, which is articulated to them and which is preferably connected to the slider via a connecting slider. In this way, it is possible to drive both the slider and the rotor elements with a single drive element, thus eliminating the need for additional effort for any synchronization of different drive elements.

It is particularly advantageous in this context if the rotor elements are each driven by a connecting rod and preferably each connected to the slider by a connecting slider. This ensures symmetrical force application.

An optimum sequence of the individual movements is achieved in particular in that the connecting slide(s) is/are firmly connected to the slider and that an elongated hole is arranged at each connecting slider, in which a pin of the connecting rod engages.

The elongated hole ensures that in a first phase of the forward movement only the slider is advanced, while the pin of the connecting rod slides backwards in the elongated hole of the connecting slider so that the connecting rod and thus the rotor elements are not moved. This phase is completed when the cone has arrived at the rear end of the elongated hole. In a second phase of the forward movement, the connecting slider now takes the connecting rod with it and in this way causes the rotor elements to rotate.

During the backward motion, at first only one movement of the slider can be observed in an analogous manner, while the pin of connecting slider glides ahead within the elongated hole, so that here too no movement of the connecting rod and rotor elements occurs. Only when the pin is in contact with the front end of the elongated hole will the connecting rod be entrained and the rotor elements are turned back.

A particularly preferred embodiment variant of the present invention provides that a slider is movably arranged on the side of the main sections of the tissue staples facing away from the engagement sections in the direction of the longitudinal axis, which slider has two lateral feed regions at its front end face, between which a substantially rectangular recess is provided, and that a retaining element is provided which engages in the recess of the slider in order to deform the linear main section of an interposed tissue staple when the slider is advanced.

It is an important aspect of this invention that the slider can both feed the tissue staples and deform them in a single movement. It is advantageous that the force on the respective tissue staple is exerted directly in the area of the engagement elements during the feed so that these can be advanced against the resistance of the body tissue without first causing a deformation of the tissue staple. Only when the tissue staple has penetrated sufficiently deeply into the body tissue does the middle section of the main section of the tissue staple come into contact with the retaining element, so that the tissue staple is bent around the edges of the retaining element.

After the tissue staple has been properly placed in the body tissue, a safe detachment from the device according to the invention must be ensured. In accordance with a preferred embodiment variant of the present invention, this is achieved by arranging an ejection spring in such a way that it removes a deformed tissue staple from the retaining element. A particular advantage of this solution is that the tissue staple is stripped fully automatically, without any special control effort.

Stripping is achieved in a particularly simple way in that the ejection spring protrudes into the movement area of the slider in a force-free state. By pushing the slider forward, the ejection spring is pretensioned and by pulling the slider back, the spring is released to strip off the tissue staple.

A particularly safe guidance of the tissue staple can be achieved by providing a lug on the slider which supports the tissue staple to be advanced against the pretension of the ejection spring.

An optimal configuration of the tissue staple in the applied state is achieved in that the recess is essentially rectangular.

A particularly compact and space-saving design of the device according to the invention can be achieved in that the slider is formed in a plate-shaped manner and the range of movement of the slider lies in a plane which lies in the storage position in the region of the tips of the engagement sections of the tissue staples, and particularly preferably lies substantially parallel and at a constant distance from the main sections of the tissue staples in the storage position. In this way it is possible that the slider and other components used to drive the slider use the space that is defined by the tissue staples in the storage position in the magazine.

A particularly efficient operation of the device is achieved in that the slider has a front position and a rear position, wherein in the front position a deformed tissue staple is clamped between the slider and the retaining element, and in the rear position a tissue staple rotated from the storage position to a working position perpendicular thereto is receivable.

An important aspect of the present invention is provided in particular that a hydraulic cylinder and/or a piston rod are arranged at least partially inside the space between the engagement sections of the tissue staples in the storage position, and preferably that the piston rod is fixedly connected to the slider.

The hydraulic drive via a hydraulic cylinder, which enables the necessary forces to be applied independently of the distance to an operating element, is essential here. Since the tissue staples partially surround the hydraulic cylinder or the piston rod in the storage position, a special level of space saving is achieved.

In particular, the device can be made particularly compact in that the hydraulic cylinder is formed in a double-acting manner.

A particularly favored embodiment variant of the invention provides at least one channel for accommodating an instrument. Such known holding instruments can be advantageously used to hold tissue or to manipulate its position in order to be able to use the tissue staples optimally.

Preferably, two channels are provided, which preferably diverge slightly towards the front, wherein the angle between the channels is particularly controllable. This allows more distant tissue to be pulled up appropriately.

In particular, the manipulation of body tissue can be made particularly flexible if the holding instruments can be controlled independently of each other.

A particularly compact construction of the device according to the invention can be achieved in particular in that the channel is preferably arranged adjacent to the hydraulic cylinder and/or that the channel is arranged between the side parts.

It is particularly advantageous if the channel is located in the proximal area of the head part. This leaves space underneath the tissue staples in their storage position, so that the holding instruments can be pushed forward from the divergent channels to the side, even outside the cross-section of the device, in order to be able to also grasp lateral areas of the body tissue and pull them into the area of the tissue staples.

BRIEF DESCRIPTION OF THE DRAWINGS

In the following, embodiment examples of the present invention will be explained in more detail using the attached figures, wherein:

FIG. 1 shows a first embodiment variant of a device according to the invention in a view from below;

FIG. 2 shows the device of FIG. 1 in a side view;

FIG. 3 shows the device of FIG. 1 and FIG. 2 in one in a view from above;

FIG. 4 shows the device from FIG. 1 to FIG. 3 in one in a front view;

FIG. 5 shows the device from FIG. 1 to FIG. 4 in an exploded view;

FIG. 6 to FIG. 9 show longitudinal sections at different stages of movement to explain the function of the device;

FIG. 10 and FIG. 11 show different diagonal views of a first embodiment variant of the rotor element;

FIG. 12 and FIG. 13 show different oblique views of a second embodiment variant of the rotor element;

FIG. 14 shows a further embodiment variant of a device according to the invention in a longitudinal section;

FIG. 17 and FIG. 18 each show a longitudinal section of a further embodiment variant of the invention in two different positions.

DETAILED DESCRIPTION

Figure 15:
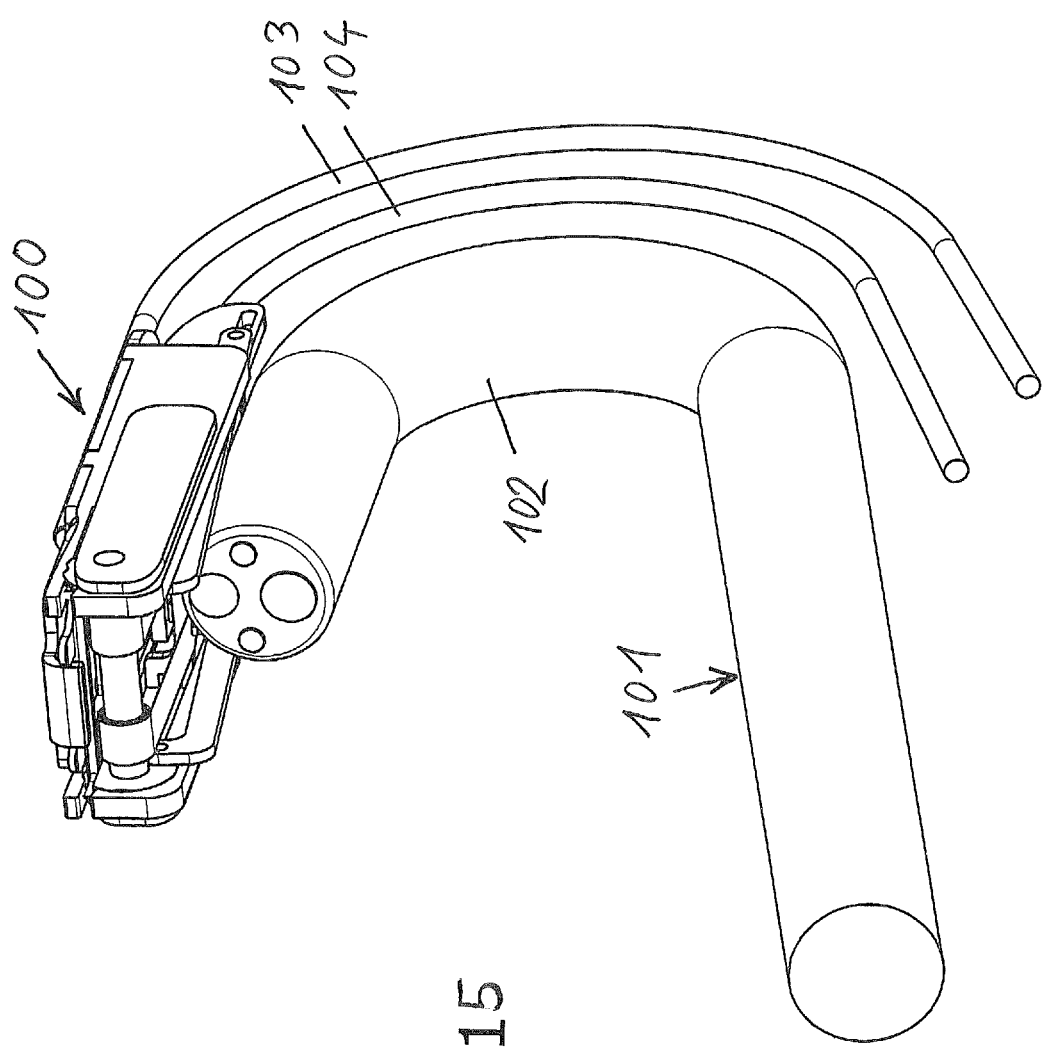
FIG. 15 and FIG. 16 show two alternative application possibilities of the device each in a diagonal view.

FIG. 1 to FIG. 5 show the head part 100 of a device according to the invention, which can eject and deform a tissue staple 1 with a linear main section 2 and two parallel engagement sections 3 (visible in FIG. 5) projecting vertically from it.

The device has a support element 4 on which two side parts 5, a hydraulic cylinder 6 with a cylinder rod 10 and a retaining element 22 are arranged. On support element 4, tissue staples 1 with their engagement sections 3 rest in a storage position 7, which is partially illustrated in FIG. 2.

The side parts 5 each have a recess 39, the main part of which is rectangular and is intended to receive the engagement sections 3 of the tissue staples 1 in the storage position 7 and to guide them up and down. In addition, the respective rotor element 9 is accommodated in the recess 39.

In storage position 7, the tissue staples 1 are essentially stacked on top of each other, wherein the planes 7a, in which the main section 2 and the engagement sections 3 are located, are parallel to each other. In addition, the planes 7a are essentially perpendicular to the axis 6a of the hydraulic cylinder 6, which is also the longitudinal axis of the device. This enables the tissue staples 1 to be arranged in storage position 7 in such a way that the space formed between the engagement sections 3 of the tissue staples 1 in storage position 7 can at least partially contain the hydraulic cylinder 6 or the cylinder rod 10. This enables a very compact and space-saving design.

The tissue staples 1 in storage position 7 are pressed by a storage slider 8 against two rotor elements 9 which are connected to a shaft 12. The pretension required for this is generated by two storage springs 11. These are designed as unwound spiral springs, one end each is attached to the shaft 12, the other ends to the storage slider 8.

Each of the two rotor elements 9 is rotatably mounted and has a bearing surface 13 with a support lug 16 for an engagement section 3 of a tissue staple 1 and a recess 14. A rotor spring 15 can engage in the recess 14 to allow latching to define positions of the rotor elements 9. The rotor spring 15 is designed as an extension of the side part 5.

A slider 17 is attached to the cylinder rod 10 and has two feed regions 19 with lugs 18. There is a central rectangular recess 20 between the feed regions 19. The slider 17 can be moved along the longitudinal axis 6a via the hydraulic cylinder 6.

In a first orientation of the rotor elements 9, the bearing surfaces 13 face in the direction of the tissue staples 1 in storage position 7. The storage slider 8 presses in this case a first tissue staple 1 against the bearing surfaces 13. Now the rotor elements 9 can be turned by about 90°. The tissue staple 1 resting thereon is co-rotated by the support lugs 16 to reach a working position 29, in which it is arranged in a further plane 29a, which is parallel to the longitudinal axis 6a. During the first part of the rotation, the first tissue staple 1 is pressed against the bearing surfaces 13 by the storage slider 8, during the second part of the rotation, the surface pressure is maintained by the rotor spring 15 in order to hold the first tissue staple 1 in a defined position. The hydraulic cylinder 6 is at this time in a retracted position, the slider 17 is therefore behind the main section 2 of the first tissue staple 1.

Now the hydraulic cylinder 6 can be extended. The slider 17 takes the first tissue staple 1 with it. The position on slider 17 is secured by an ejection spring 21 pressing the first tissue staple 1 against the lug 18. At the same time, the ejection springs 21 are increasingly pretensioned by the feed.

The first tissue staple 1 is now pressed against the retaining element 22, which is centered and adapted to the width of the recess 20 of the slider 17. This deforms the first tissue staple 1 on the main section 2 into a rectangle.

When the hydraulic cylinder 6 is subsequently retracted, the pretension of the ejection spring 21 is transferred to the first tissue staple 1 and thus stripped off by the retaining element 22.

The rotor elements 9 are each rotated by a connecting rod 23 articulated to them, which has a first pin 30, which engages in an eccentric bore 31 of the respective rotor element 9. One connecting slider 24 each connected to slider 17 has an elongated hole 25 in which a second pin 26 of the connecting rod 23 engages. The connection in an elongated hole 25 ensures that the rotation of the rotor elements 9 takes place in a second phase of the movement of the slider 17.

In the following, the other components of the device according to the invention are briefly explained:

Cover plates 32 are fitted laterally outside the side parts 5 to cover their recesses 33. The cylinder rod 10 is sealed by seals 34 against the hydraulic cylinder 6, which is fastened to the support element 4 by mounting elements 35. Hydraulic connections 36 and 37 are used to supply the hydraulic medium to control the device. A mounting bracket is designated with reference numeral 38.

To illustrate the operation of the device, FIGS. 6 to 9 show the same longitudinal section in different positions of the hydraulic cylinder 6.

FIG. 6 shows the initial condition with hydraulic cylinder 6 with fully extended cylinder rod 10. Pin 26 is in the extension-side stop 27 of elongated hole 25, the bearing surface 13 of the rotor elements 9 is parallel to the longitudinal axis 6a. The slider 17 is in the fully extended position in which a tissue staple 1 (not shown here) has just been ejected.

Starting from this position, the cylinder rod 10 is retracted, the slider 17 moves to the right in the diagram, the connecting slider 24 connected to it also moves with it. In the first part of the extension process, no movement is transmitted to the connecting rod 23, since the pin 26 moves in the direction of the stop 28 on the entry side of the elongated hole 25 of the connecting slider 24. After about half the stroke, the stop 28 on the entry side is reached, and the connecting rod 23 is now moved with the slider 17 and the connecting slider 24. In this way the rotor elements 9 are turned by about a right angle so that a first tissue staple 1, which lies on the bearing surfaces 13 in the storage position, is turned from a vertical position in FIG. 6 to a horizontal position in which it lies in the plane of the slider 17. The tissue staple 1, which rests on the bearing surfaces 13, is entrained by the support lugs 16 of the rotor elements 9. Since the slider 17 has already retracted behind the rotor elements 9 at this point, the movement path for the tissue staple 1 is free.

The position thus achieved with the cylinder rod 10 fully retracted is shown in FIG. 7. Now the cylinder rod 10 can be extended again from the hydraulic cylinder 6. The slider 17 moves again with the connecting sliders 24 in the direction of the position of FIG. 6. Again initially no movement is transmitted to the connecting rods 23, as the pin 26 is pushed in the elongated hole 25 in the direction of the stop 27 on the extension side. When the stop 27 on the extension side is reached, as shown in FIG. 8, the connecting rods 23 move with the cylinder rod 10, whereby the rotor elements 9 are turned back to the position shown in FIG. 6, which corresponds to the position shown in FIG. 10. During the extension movement of the cylinder rod 10, which starts from FIG. 7 and ends in FIG. 9, the slider 17 is pushed forward to deform and eject the tissue staple 1 inserted in the phase between FIG. 6 and FIG. 7. In the position shown in FIG. 9, the rotor elements 9 are again in the position to receive another tissue staple 1.

When the slider 17 is fed, the ejection springs 21 are pretensioned via the tissue staple 1 in working position 29, wherein the lugs 18 on the slider 17 support the tissue staple 1 in working position 29 at the bottom, so that the tissue staple 1 is guided on both sides. When pulling back the slider 17, the support of the tissue staple 1 from below is omitted so that the ejection springs 21 push it downwards and strip it off from the retaining element 22.

The working cycle can be restarted after reaching the position shown in FIG. 9.

FIG. 10 to FIG. 13 show two different embodiment variants of a rotor element 9. The first embodiment variant shown in FIG. 10 and FIG. 11 corresponds to the rotor element 9 used and shown in the embodiment variants of FIG. 1 to FIG. 9.

This first embodiment variant has a bearing surface 13, which forms part of a circular segment in relation to circumference 43. A lug 13a is provided at one end to entrain the tissue staple 1, which in its storage position rests with its engagement section 3 against the bearing surface 13, when the rotor element 9 is rotated. The bearing surface 13 does not extend over the entire thickness of the rotor element 9. A web 40 remains on one side, which guides the engagement section 3 of the adjacent tissue staple 1 laterally. In the region of this web 40, a first recess 41 is provided and, as viewed from the center of rotor element 9, a second recess 14 is designed on circumference 43 at a right angle thereto. The two recesses 41, 14 are used to latch the rotor spring 15 and to determine the end positions of the rotation of the rotor element 9. The eccentric bore 31 is used for rotation through the connecting rod 23. The bore 42 is intended for fitting onto the shaft 12.

In the alternative embodiment variant shown in FIG. 12 and FIG. 13, the bearing surface 13 extends over the entire thickness of the circumference 43. The lateral guidance is assumed by the cover plates 32. In addition to the bearing surface 13, a further contact surface 44 at right angles to the circumference is preferably provided, against which the tissue staples 1 rest in the storage position 7 when the bearing surface 13 is turned into the ejection position (parallel to the longitudinal axis 6a). With this embodiment variant, the engagement sections 3 of the tissue staples 1, which rest against the bearing surface 13 or the contact surface 44 and are pressed on by the storage springs 11, define the end positions of the rotation of the rotor element 9. Therefore, recesses are not required here.

FIG. 14 shows a longitudinal section of an embodiment variant of the device according to the invention using the rotor elements 9 of FIG. 12 and FIG. 13. This variant largely corresponds to the embodiment variant shown in FIG. 1 to FIG. 9. It can be seen that the engagement section 3 of a first tissue staple 1 on the bearing surface 13 is already present in the working position 29. A further tissue staple 1 with its engagement section 3 rests on the further contact surface 44 and is pressed against it by the storage slider 8 so that the rotor element 9 is fixed in this position in a resilient manner. After ejecting the first tissue staple 1, the rotor element 9 is turned back clockwise, wherein the storage slider 8 together with the tissue staples 1 in storage position 7 must first be pushed back against the resistance of the storage springs 11 however.

FIG. 14 also shows that the engagement sections 3 of the tissue staples 1 in the storage position 7 (a tissue staple 1 is shown with interrupted lines correspondingly) extend upwardly well beyond the lower section of the cylinder rod 10, which means that in the extended position the cylinder rod 10 moves within the rectangular space spanned on three sides of the main section 2 and the two engagement sections 3 of the tissue staple 1.

FIG. 15 shows a first variant of the use of a device according to the invention. The head part 100 is detachably mounted on a standard endoscope 101 with a bent portion 102 and is controlled by hydraulic hoses 103 and 104, which are inserted into a body opening parallel to the endoscope.

Figure 16:
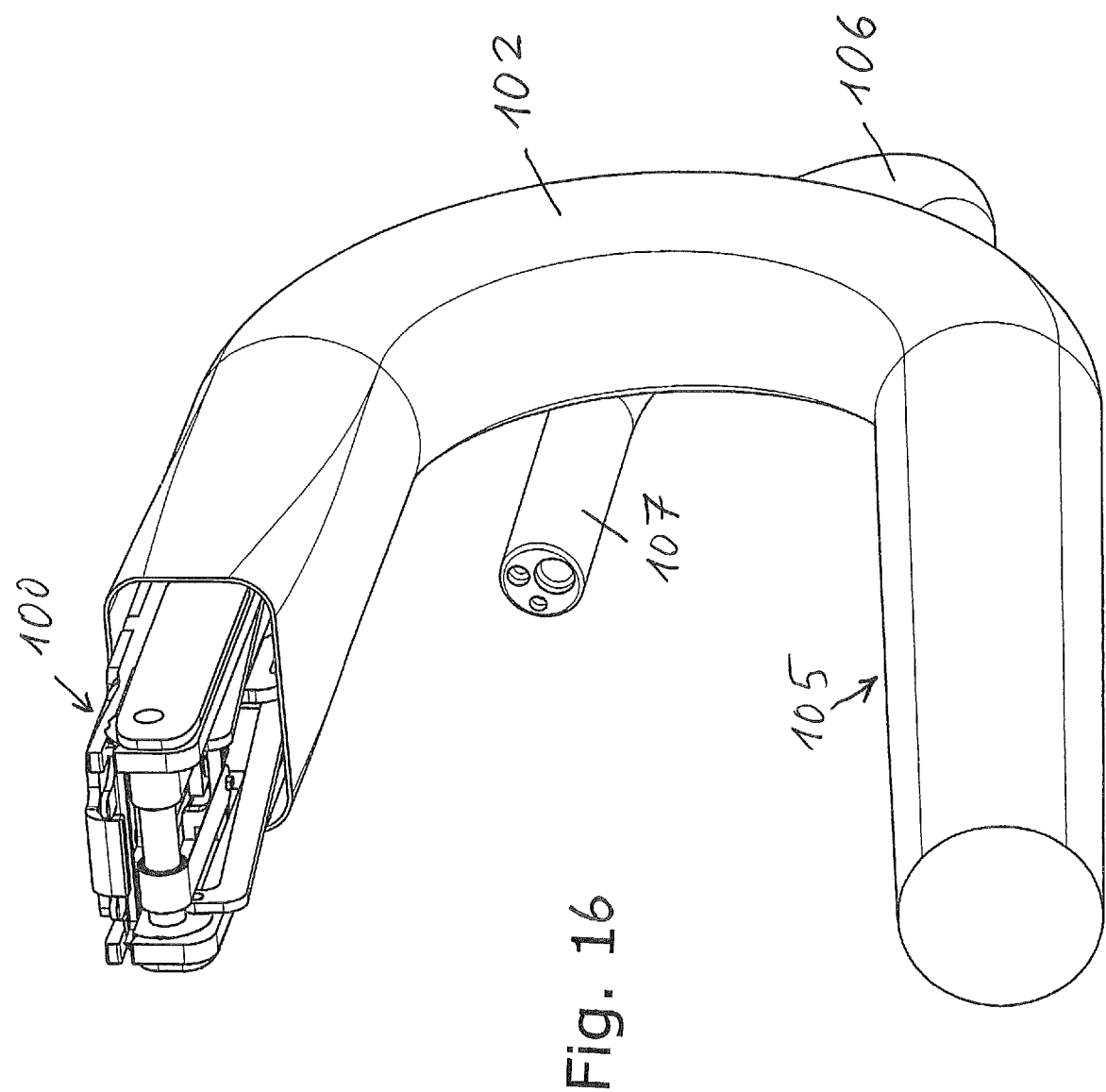
Figure 19:
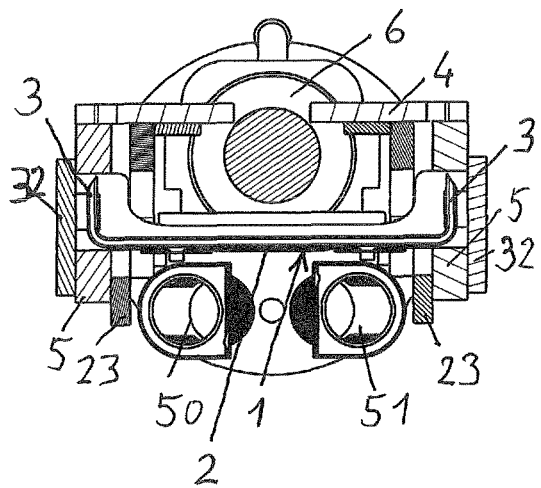
FIG. 19 shows a cross-section through the embodiment variant of FIG. 17 and FIG. 18.
Figure 20:
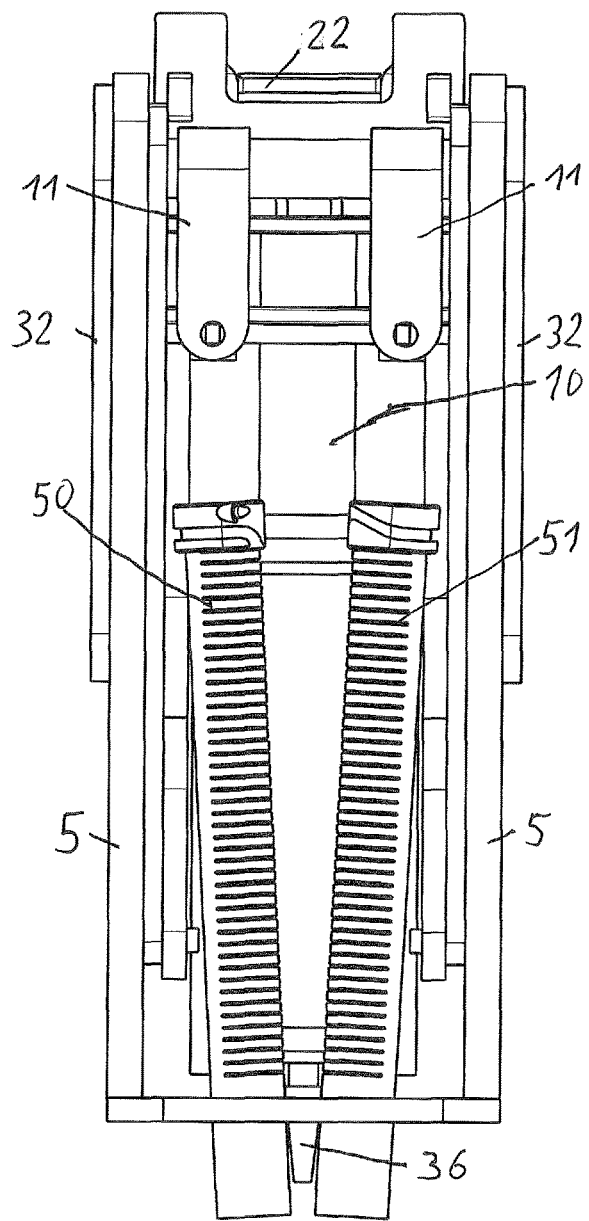
FIG. 20 shows a view of the embodiment variant from FIG. 17 to FIG. 19 from below.

FIG. 16 shows an alternative variant of the use of the device according to the invention, in which the head part 100 forms the tip of an independent flexible instrument 105. According to standard designs has at least one channel through which an endoscope 107 with a bent portion 102 can be inserted. The endoscope 107 is led out laterally with a separate bent portion 106 in order to be able to observe the process of stapling.

The embodiment variant of FIG. 17 and FIG. 18 differs from the variants described above in that two channels 50, 51 are provided below the hydraulic cylinder 6. Channels 50, 51 are directed outwards towards the distal end, i.e. divergent, wherein the angle of divergence is preferably adjustable. If holding instruments are now pushed through the channels 50 and 51 forward in each case, then these come out slightly directed outwards, wherein thus the variable extension increases by the distance to the point, thus increasing the space underneath the tissue staples 1 in their storage position 7.

Due to the special design of the device, it is possible to arrange the channels 50 and 51 within the circular cross-section defined by the other components.

The present invention makes it possible to connect tissues inside the body with tissue staples, wherein it is particularly advantageous that a number of tissue staples can be used one after the other without the need to pull the device out of the patient's body and then reinsert it again.

The invention claimed is:

1. A device for connecting body tissues, the device comprising:
   a head part configured and arranged to be extended into a body opening, the head part including a longitudinal axis;
   a plurality of tissue staples accommodated in the head part in a storage position (7), the tissue staples including
      a linear main section, and
      two engagement sections projecting perpendicularly from the linear main section and each of the two engagement sections are aligned in a first plane substantially perpendicular to the longitudinal axis;
   two rotor elements configured and arranged to pivot about an axis parallel to the main sections of the plurality of tissue staples, and each of the rotor elements including a bearing surface configured and arranged to engage a respective engagement section of one of the plurality of tissue staples in order to rotate said tissue staple from the storage position into an operating position in which the tissue staple is arranged in a further plane which is oriented substantially perpendicularly to the first plane; and a slider configured and arranged to advance the tissue staple, which is present in the working position, in the further plane and to deform it into a clamping position about body tissue.

2. The device according to claim 1, further including a rotor spring configured and arranged to engage with at least one of the two rotor elements in order to carry out its movement in two rotational positions so as to be latchable, and wherein the two rotor elements are connected to one another by a shaft.

3. The device according to claim 2, characterized in that the tissue staples in the storage position are pretensioned against the rotor element by at least one storage spring via a storage slider, and wherein the storage spring is fastened to the shaft of the rotor elements.

4. The device according to claim 1, characterized in that the rotor elements are configured and arranged to be driven by at least one connecting rod which is articulated to the rotor elements, and the at least one connecting rod is connected to the slider via a connecting slider.

5. The device according to claim 1, characterized in that the rotor elements are configured and arranged to each be driven by a connecting rod, and the rotor elements are each connected to the slider via a connecting slider.

6. The device according to claim 4, characterized in that the connecting slider is firmly connected to the slider, and each connecting slider includes an elongated hole configured and arranged to engage with a pin of the connecting rod.

7. The device according to claim 1, characterized in that the tissue staples are guided, in the storage position, by recesses in side parts.

8. The device according to claim 1, characterized in that at least one of the two rotor elements has a contact surface which is at a right angle to the bearing surface.

9. The device according to claim 1, characterized in that the slider is arranged on the side of the main section of the plurality of tissue staples, and facing away from the engagement sections so as to be movable in a direction of the longitudinal axis, said slider including two lateral feed regions on its front end face, between which a recess is provided, the recess including a retaining element configured and arranged to engage in the recess of the slider in order to deform the linear main section of an interposed tissue staple when the slider is advanced.

10. The device according to claim 9, further including an ejection spring configured and arranged to strip off a deformed tissue staple from the retaining element.

11. The device according to claim 10, characterized in that the ejection spring is further configured and arranged to project, in a force-free state, into a range of movement of the slider.

12. The device according to claim 10, characterized in that the ejection spring is configured and arranged to be pretensioned during advance of the slider and transfers the pretension to the tissue staple during a return stroke of the slider.

13. The device according to claim 10, further including a lug on the slider, the lug configured and arranged to support the advancing tissue staple against the pretension of the ejection spring.

14. The device according to claim 9, characterized in that the recess is substantially rectangular.

15. The device according to claim 9, characterized in that the slider is plate-shaped and the range of movement of the slider lies in the further plane which lies, while in the storage position, in a region of the tips of the engagement sections of the tissue staples, and further lies substantially parallel and at a constant distance from the main sections of the tissue staples.

16. The device according to claim 10, characterized in that the slider includes a front position and a rear position, wherein the deformed tissue staple in the front position is configured and arranged to be clamped between the slider and the retaining element, and a tissue staple in the rear position is configured and arranged to be turned from the storage position into a working position and disposed perpendicular thereto is receivable.

17. The device according to claim 1, wherein at least partially arranged within the space disposed between the engagement sections of the tissue staples in the storage position is a hydraulic cylinder and/or a piston rod, and the piston rod is fixedly connected to the slider.

18. The device according to claim 17, characterized in that the hydraulic cylinder is double-acting.

19. The device according to claim 1, characterized in that the head part is configured and arranged to be attached to an endoscope.

20. The device according to claim 17, characterized in that the head part is integrally connected to a flexible instrument including a channel configured and arranged for mounting to an endoscope.

21. The device according to claim 20, further including at least one channel configured and arranged to receive a holding instrument.

22. The device according to claim 21, wherein the at least one channel includes two channels configured and arranged to diverge slightly towards a front of the device, wherein the angle between the two channels is controllable.

23. The device according to claim 22, wherein the two channels are configured and arranged to receive more than one holding instrument, and each of the holding instruments are controllable independently of one another.

24. The device according to claim 20, characterized in that the channel is arranged adjacent to the hydraulic cylinder.

25. The device according to claim 21, characterized in that the at least one channel is arranged between side parts.

26. The device according to claim 21, characterized in that the at least one channel is arranged in a proximal region of the head part.

* * * * *